United States Patent [19]

Tsao

[11] 4,039,597
[45] Aug. 2, 1977

[54] CARBON DIOXIDE REMOVAL FROM CHLORINATED HYDROCARBON PRODUCTION SYSTEM

[75] Inventor: Utah Tsao, Jersey City, N.J.

[73] Assignee: The Lummus Company, Bloomfield, N.J.

[21] Appl. No.: 602,388

[22] Filed: Aug. 6, 1975

Related U.S. Application Data

[63] Continuation-in-part of Ser. No. 547,377, Feb. 6, 1975, abandoned.

[51] Int. Cl.$^2$ .................. C07C 19/00; C07C 21/00; C07C 17/02; C07C 17/10
[52] U.S. Cl. .................. 260/654 A; 260/652 P; 260/654 S; 260/659 R; 260/659 A; 260/662 A; 423/437
[58] Field of Search .......... 260/659 A, 659 R, 654 A, 260/662 A, 652 P, 654 S; 55/68

[56] References Cited

U.S. PATENT DOCUMENTS

| 2,395,314 | 2/1946 | Blumer | 260/659 A X |
|---|---|---|---|
| 2,498,552 | 2/1950 | Kilgren et al. | 260/659 A |
| 2,540,905 | 2/1951 | Neubauer et al. | 260/659 A |
| 3,148,041 | 9/1964 | Dehn et al. | 55/31 |
| 3,449,450 | 6/1969 | Bohl et al. | 260/654 |
| 3,488,398 | 1/1970 | Harpring et al. | 260/659 A |
| 3,496,242 | 2/1970 | Berkowitz et al. | 260/664 |
| 3,551,506 | 12/1970 | Weinstein | 260/656 |
| 3,637,895 | 1/1972 | Riegel et al. | 260/659 A |
| 3,923,913 | 12/1975 | Antonini et al. | 260/654 H |
| 3,980,723 | 9/1976 | Riegel | 260/654 A |

FOREIGN PATENT DOCUMENTS

| 928,472 | 6/1963 | United Kingdom | 55/68 |

OTHER PUBLICATIONS

Kirk-Othmer, "Encyclopedia of Chemical Technology," vol. 2, pp. 274 to 280 (1963).

Primary Examiner—Floyd D. Higel
Attorney, Agent, or Firm—Marn & Jangarathis

[57] ABSTRACT

In the production of chlorinated hydrocarbons, a gas stream containing unreacted hydrocarbon, carbon dioxide, and chlorinated hydrocarbon(s) is contacted with an acid gas absorption solution to absorb carbon dioxide, with the absorption solution being stripped of any absorbed chlorinated hydrocarbon, preferably by use of feed hydrocarbon as stripping gas, without stripping of carbon dioxide therefrom, to maintain the rich absorption solution introduced into the carbon dioxide stripper essentially free of absorbed chlorinated hydrocarbons.

10 Claims, 1 Drawing Figure

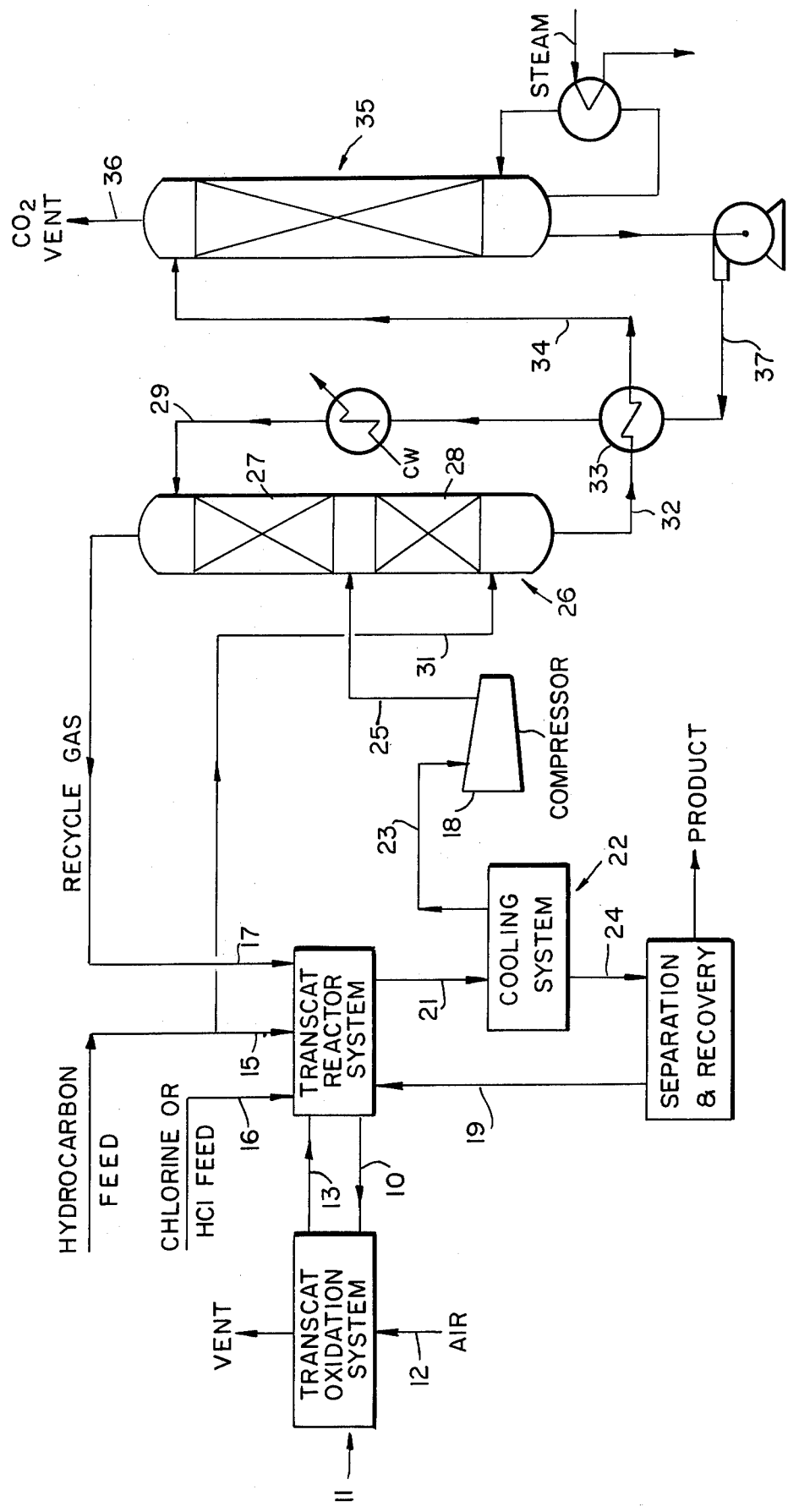

CARBON DIOXIDE REMOVAL FROM CHLORINATED HYDROCARBON PRODUCTION SYSTEM

This application is a continuation-in-part of U.S. Application Ser. No. 547,377, filed on Feb. 6, 1975 and now abandoned.

This invention relates to the production of chlorinated hydrocarbons, and more particularly, to a new and improved process for removing carbon dioxide from an effluent withdrawn from a chlorinated hydrocarbon production zone.

In the production of chlorinated hydrocarbons by an oxychlorination type of process, a portion of the hydrocarbon feed is oxidized to carbon dioxide, and such carbon dioxide must be removed from the system in order to prevent a build-up thereof.

An object of the present invention is to provide an improved process for producing chlorinated hydrocarbons.

Another object of the present invention is to provide for removal of carbon dioxide from a system for producing chlorinated hydrocarbons.

These and other objects of the present invention should be more readily apparent from reading the following description thereof.

In accordance with the present invention, there is recovered from an effluent withdrawn from a chlorinated hydrocarbon production zone, a gaseous stream which contains unreacted hydrocarbon, carbon dioxide in a manner amount of at least one chlorinated hydrocarbon. The gaseous stream is contacted with an acid gas absorption solution to absorb carbon dioxide therefrom, with the solution being stripped of chlorinated hydrocarbon prior to introduction thereof into the carbon dioxide stripper, to maintain the absorption solution introduced into the carbon dioxide stripper essentially free of chlorinated hydrocarbon. It has been found that by effecting such stripping, the useful life of the absorption solution is increased. In general, the amount of chlorinated hydrocarbons, as measured by the amount of chlorinated hydrocarbon released in the vent from the carbon dioxide stripper, is less than 100 ppm and preferably less than 50ppm.

The hydrocarbon in the gas stream withdrawn from the carbon dioxide absorption zone is recycled to the chlorinated hydrocarbon production zone. The carbon dioxide rich absorption solution is passed to a regeneration zone (carbon dioxide stripper) to strip carbon dioxide therefrom and recover a lean absorption solution for recycle to the carbon dioxide absorption zone.

The acid gas absorption solution employed for absorbing the carbon dioxide may be any one of the wide variety of absorption solutions which are known to absorb carbon dioxide. As representative examples of such absorption solutions, there may be mentioned: amine absorption solutions, including alcohol amines; carbonates, including organic and inorganic carbonates; sulfolanes; dioxolanes, etc. The absorption solution is preferably a carbonate and particularly an alkali metal carbonate (sodium or potassium carbonate).

The stripping of the carbon dioxide rich absorption solution is preferably effected by the use of a stripping gas, with the stripping gas preferably being the hydrocarbon which is to be employed as feed to the chlorinated hydrocarbon production zone. It is to be understood, however, that a stripping gas other than the hydrocarbon feed could be employed, provided the stripping gas does not adversely affect the carbon dioxide absorption. The hydrocarbon feed gas, however, is the preferred stripping gas in that in this manner no extraneous components need be introduced into the system in order to effect the stripping. It is to be understood, however, that stripping could be effected without the use of a stripping gas, e.g., by providing bottoms reboil, although the use of a stripping gas is preferred; in particular, the hydrocarbon used as feed to the chlorinated hydrocarbon production zone.

The absorption of the carbon dioxide and stripping of the dissolved chlorinated hydrocarbon from the carbon dioxide absorption solution, prior to carbon dioxide stripping, can be effected in a single vessel, with the bottom portion of the vessel functioning as a stripping section for stripping dissolved chlorinated hydrocarbons. As a result, the feed gas, essentially free of carbon dioxide, stripped chlorinated hydrocarbon and stripping gas are withdrawn as a single stream from the absorber. Alternatively, the absorption of carbon dioxide and stripping of dissolved chlorinated hydrocarbon can be effected in separate vessels or in separate sections of the same vessel, with the carbon dioxide rich absorption solution from the absorber being introduced into the separate stripping section or vessel, prior to introduction into the carbon dioxide stripper. In the use of such separate vessels or sections, the gas stream recovered from both the carbon dioxide absorption and chlorinated hydrocarbon stripping are introduced into the chlorinated hydrocarbon production zone.

The carbon dioxide absorber is generally operated at a temperature from about 110° F to about 160° F, preferably from about 120° F to about 140° F, and a pressure from about 50 psig to about 500 psig, preferably from about 75 psig to about 100 psig. It is to be understood that the hereinabove described conditions are illustrative, and the selection of optimum conditions for absorbing carbon dioxide by use of a carbonate absorption solution while effecting stripping to maintain the rich absorption solution essentially free of chlorinated hydrocarbons is deemed to be within the scope of those skilled in the art from the teachings herein. It is to be understood that in the case where the stripping of chlorinated hydrocarbons from the carbon dioxide rich absorption solution (without stripping of carbon dioxide) is effected in a separate vessel or section, the stripping can be effected at conditions different than those prevailing in the absorber; e.g., lower pressure.

Subsequent to the stripping of any dissolved chlorinated hydrocarbon from the carbon rich absorption solution, the rich absorption solution is introduced into a carbon dioxide stripper, as known in the art to recover a lean absorption solution for recycle to the carbon dioxide.

The gaseous stream, containing hydrocarbon, carbon dioxide and one or more chlorinated hydrocarbons, to be employed as feed to the carbon dioxide absorption zone may be separated from the chlorinated hydrocarbon effluent by any one of a wide variety of procedures. In general, the chlorinated hydrocarbon effluent also includes water vapor and a convenient method of separating the water vapor from the effluent gas is by cooling to condense water vapor therefrom, with such cooling also generally resulting in the condensation of heavier chlorinated hydrocarbon components from the gaseous effluent, whereby a gaseous stream containing methane, inerts, carbon dioxide and generally also lighter chlorinated hydrocarbons; is recovered from the cooling operation. All or a portion of this gaseous stream may be employed as feed to the carbon dioxide absorption system. In general, such a gaseous stream can be recovered by cooling the chlorinated hydrocarbon effluent in one or more cooling stages (which can be indirect cooling stages or direct quench cooling) to a temperature from about 110° F to about 10° F, at pressures from about 30 psig to about 200 psig.

Although the above operation is preferred, it is to be understood that the gaseous stream containing hydrocarbon, carbon dioxide and chlorinated hydrocarbon(s) can be recovered by other means; e.g., fractionation. It is also to be understood that in such recovery operations, the gaseous feed to the carbon dioxide absorption system can be free of inerts, such as carbon monoxide and nitrogen; e.g., inerts can be removed, prior to introduction of the gas containing hydrocarbon, carbon dioxide and chlorinated hydrocarbon(s) into the carbon dioxide absorption system; however, in general, some amounts of inerts are present in the gas feed to the carbon dioxide absorption zone.

The chlorinated hydrocarbon effluent may be produced by any one of a wide variety of oxychlorination processes known in the art, which, as known in the art, are effected in the presence of a Deacon or oxychlorination type of catalyst. The general processes for producing chlorinated hydrocarbons by oxychlorination are well-known in the art and no detailed description thereof is deemed necessary for a complete understanding of the present invention.

Although the process of the present invention is generally applicable to the oxychlorination of hydrocarbons, the process is particularly suitable for the oxychlorination of $C_1 - C_4$ aliphatic hydrocarbons (both saturated and olefinically unsaturated), and in particular, to the oxychlorination of methane to produce chlorinated methane(s); and ethane and/or ethylene to produce chlorinated $C_2$ hydrocarbons. In accordance with such a process, a molten mixture, containing cuprous chloride, cupric chloride and a suitable melting point depressant; in particular, potassium chloride, is contacted with molecular oxygen, in a first reaction (oxidation) zone, to produce copper oxychloride. A molten mixture, containing cuprous chloride, cupric chloride and coppr oxychloride, withdrawn from the first reaction zone is contacted in a second reaction (oxychlorination and chlorination) zone with hydrocarbon and hydrogen chloride and/or chlorine to produce chlorinated hydrocarbon. The feed to the second reaction zone, as required, generally also includes chlorinated hydrocarbon as recycle. Molten salt from the second reaction zone is then recycled to the first reaction zone.

In general, the second reaction zone is operated at a temperature from 700° F to 1200° F., preferably 700° F to 950° F, with higher selectivity being obtained at temperatures from 700° F to 860° F., preferably 800° F to 850° F. The operating pressures are generally in the order of 1 to 10 atm.

The first reaction (oxidation) zone is generally operated at temperatures from 700° F to 950° F, and preferably from 800° F to 900° F, with the operating pressure generally being in the order of 1 to 10 atm.

The chlorinated hydrocarbons which are recycled to the oxychlorination reaction zone are determined by the desired reaction product. As should be apparent, if all chlorinated hydrocarbons are desired as product in the proportions produced there need be no recycle of chlorinated hydrocarbon. In the production, for example, of vinyl chloride by the use of ethane and/or ethylene, 1,2-dichloroethane produced in the oxychlorination is recovered and dehydrochlorinated in a separate reaction zone.

Particular processes for producing chlorinated methanes by the use of molten salts are described in U.S. application Ser. No. 299,848, filed Oct. 24, 1972 and U.S. application Ser. No. 299,114 filed Oct. 19, 1972, both of which are hereby incorporated by reference.

Particular processes for chlorination (oxychlorination) ethane and/or ethylene by the use of molten salts are described in U.S. application Ser. No. 153,374 filed on June 15, 1971, now U.S. Pat. No. 3,937,344 and U.S. application Ser. No. 157,496 filed on June 28, 1971 now U.S. Pat. No. 3,879,482, all incorporated by reference.

Referring now to the drawing, a molten salt mixture including cuprous chloride, cupric chloride and a melting point depressant, in particular potassium chloride, in line 10, is introduced into an oxidation reaction zone 11 wherein the molten salt is contacted with molecular oxygen, introduced through line 12, to produce copper oxychloride.

A molten salt mixture, containing cuprous chloride, cupric chloride and copper oxychloride withdrawn from oxidation zone 11, through line 13 is introduced into a methane oxychlorination reaction zone 14 wherein the molten salt is contacted with fresh feed methane, introduced through line 15, hydrogen chloride, chlorine or mixtures thereof, introduced through line 16, a recycle methane stream, introduced through line 17, obtained as hereinafter described, and a recycle chlorinated methane stream, introduced through line 19. As hereinabove described, as a result of such contact, methane is oxychlorinated to chlorinated methanes.

Molten salt recovered from reaction zone 14 is recycled to oxidation reaction zone 11 through line 10.

A chlorinated methane effluent, containing chlorinated methanes, unreacted methane, water vapor, carbon dioxide and as inerts, nitrogen and carbon monoxide, is withdrawn from the reaction zone 14 through line 21 and introduced into a cooling system, schematically indicated as 22. In the cooling system 22, the effluent is cooled in one or more stages to condense water vapor therefrom. In effecting such water condensation, heavier chlorinated methanes are condensed from the effluent and there is recovered a gaseous stream comprised of methane and lighter components (carbon monoxide, carbon dioxide and nitrogen), which generally also includes some lighter chlorinated methane(s), generally methyl chloride, and some minor quantities of methylene chloride and chloroform, which is withdrawn from zone 22 through line 23.

The remainder of the chlorinated hydrocarbon effluent is withdrawn from zone 22 through line 24 and introduced into a recovery system to recover desired chlorinated methane product, and chlorinated methanes for recycle to the methane oxychlorination reaction zone through line 19.

The gaseous stream in line 23, containing methane, inerts, (carbon monoxide and nitrogen), carbon dioxide, chlorinated methane(s); in particular, methyl chloride, and generally also some minor amounts of methylene chloride and chloroform, is compressed in compressor 18, and the compressed gas in line 25 introduced into a stripper-absorber, generally indicated as 26. The stripper-absorber 26 is operated in a manner such that absorption is effected in the upper section 27 and stripping is effected in the lower section 28.

A lean acid gas absorption solution; such as a carbonate, in particular, potassium carbonate, is introduced into the upper section 27 through 29 and countercurrently contacts the gaseous stream introduced through line 25. As a result of such countercurrent contact, the carbon dioxide present in the gas stream is absorbed along with minor quantities of chlorinated methane(s).

A portion of the methane to be used as fresh feed, in line 31, is introduced as a stripping gas, into the stripping section 28 of the stripper-absorber 26 to strip absorbed chlorinated methane(s) from the absorption solution and thereby maintain the rich absorption solution withdrawn from the stripper-absorber 26 essentially free of chlorinated methane(s).

A rich absorption solution, containing absorbed carbon dioxide and essentially free of chlorinated methane(s), is withdrawn from column 26 through line 32, passed through heat exchanger 33 wherein the rich absorption solution is heated by indirect heat transfer with lean absorption solution, and introduced through line 34 into a regeneration (stripping) column 35, designed and operated to strip absorbed components from the absorption solution. Stripped carbon dioxide is vented through line 36.

A lean absorption solution is withdrawn from stripper 35 through line 37, passed through heat exchanger 33 and introduced into absorption column 26 through line 29.

A gas stream, containing unreacted methane recovered from the effluent, fresh feed methane employed as stripping gas, chlorinated methane(s) and inerts, is withdrawn from column 26 through line 17 and recycled to reactor 14.

It is to be understood that depending on the composition of the gas withdrawn from the absorber 26 and the desired products, the gas could be introduced into the separation and recovery zone to separate chlorinated methane(s) therefrom, with the methane being recycled to the reactor 14.

As a further alternative all or a portion of the gas withdrawn from the cooling system 22 can be passed to an inert removal system, prior to being introduced into the carbon dioxide absorption system. Similarly, only a portion of the carbon dioxide containing gas may be introduced into the carbon dioxide absorption system, with the remainder being utilized, as appropriate, without prior carbon dioxide removal.

Alternatively, the stream containing methane, carbon dioxide and chlorinated methane(s) may be separated from the effluent other than by a cooling process, as particularly described.

Although the process of the present invention has been particularly described with reference to the production of chlorinated methanes, it is to be understood that the process could also be employed for the chlorination (oxychlorination) of ethane and/or ethylene, with the stripping gas in such a process preferably being the ethane and/or ethylene used as fresh feed. It is also to be understood that the process is also applicable to the production of chlorinated hydrocarbons other than by the use of molten salts.

As still another alternative, the absorption of carbon dioxide and stripping of chlorinated hydrocarbon from the carbon dioxide rich absorption solution can be effected in separate vessels or sections, in which case the gaseous stream from both the absorber and stripper are introduced into zone 14.

The above modifications and others should be apparent to those skilled in the art from the teachings herein.

The invention will be further described with respect to the following example, but it is to be understood that the scope of the invention is not to be limited thereby.

EXAMPLE I

The following recycle stream obtained in a process for the chlorination (oxychlorination) of methane by the use of molten copper chlorides, is subjected to carbon dioxide absorption, at a temperature of 140° F and a pressure of 100 psig by use of 25% potassium carbonate:

| Components | Lb/Hr |
|---|---|
| $N_2$ | 74 |
| $O_2$ | 18 |
| CO | 12 |
| $CH_4$ | 743 |
| $CO_2$ | 427 |
| $CH_3Cl$ | Trace |
| $CH_2Cl_2$ | Trace |
| $CHCl_3$ | Trace |
| $CCl_4$ | 31 |
| | 1405  60.5 Lb Mol/Hr |

The carbonate solution absorbs traces of methyl chloride, methylene chloride, chloroform and 2 lb/hr of carbon tetrachloride and the concentration of carbon tetrachloride in the $CO_2$ vent will be 4,700 ppm, by weight. By stripping the carbonate solution by 3 mols/hr of methane, the $CCl_4$ in the $CO_2$ vent is reduced to about 5 ppm, by weight.

EXAMPLE II

The following stream, obtained in a process for the chlorination (oxychlorination) of ethane to produce vinyl chloride (VC) by the use of molten copper chlorides, is subjected to carbon dioxide absorption at a temperature of 140° F and a pressure of 100 psig by use of 25% potassium carbonate.

| Components | Lb/hr. |
|---|---|
| Inerts | 3,919 |
| $CO_2$ | 4,362 |
| $C_2H_4$ | 18,973 |
| $C_2H_6$ | 36,117 |
| $C_2H_2/C_3$'s | 1,367 |
| $CH_3Cl/C_4$'s | 550 |
| $C_2H_3Cl(VC)$ | 30,756 |
| $C_2H_5Cl$ | 19,989 |
| Chlorides of $C_2$'s | 2,164 |
| Chlorides of $C_1$'s | 210 |
| EDC | 327 |
| Heavy Ends | 100 |
| Water | 126 |
| | 118,960–3015.1 Lb Mol/Hr |

The carbonate solution will absorb 52 lb/hr of VC, 130 lb/hr of ethyl chloride and 62 lb/hr heavier chlorides. All these chlorides are vented to atmosphere from the $CO_2$ stripper in the $CO_2$ vent. The concentration of VC in this vent will be 12,000 ppm, by weight. If the rich carbonate solution is stripped by 30 mol/hr of the ethane which amounts to 20% of the total fresh ethane feed, the VC in the $CO_2$ vent is reduced to below 1 ppm, by weight. The ethyl chloride in the vent is reduced to 30 ppm, by weight. At the above stripping rate of ethane, about 60% of heavier chlorides remain in the rich carbonate solution. If the ethane stripping gas is increased to 120 mols/hr (about 80% of the fresh feed), then heavier chlorides in the $CO_2$ vent are reduced to 20 ppm, by weight.

The present invention is particularly advantageous in that carbon dioxide can be effectively removed from a system for producing chlorinated hydrocarbons with a longer useful life for the carbon dioxide absorption solution. In addition, the gas vented from the absorption stripper is essentially free of chlorinated hydrocarbon(s), thereby reducing losses thereof and minimizing introduction of pollutants into the atmosphere.

Numerous modifications and variations are possible in light of the above teachings and, therefore, within the scope of the appended claims, the invention may be practiced otherwise than as particularly described.

What is claimed is:

1. In a process for producing chlorinated hydrocarbons from a hydrocarbon feed in a chlorinated hydrocarbon production zone wherein an effluent is withdrawn containing chlorohydrocarbon, unreacted hydrocarbon and carbon dioxide, the improvement comprising:
   recovering from the effluent a gaseous stream comprising unreacted hydrocarbon, carbon dioxide and minor amounts of chlorinated hydrocarbons;
   contacting the gaseous stream with a carbon dioxide absorption solution to absorb carbon dioxide from the gaseous stream;
   stripping the absorption solution, containing absorbed carbon dioxide to remove chlorinated hydrocarbon therefrom to maintain the absorption solution essentially free of chlorinated hydrocarbon for introduction into a carbon dioxide stripper;
   introducing stripped absorption solution into a carbon dioxide stripper to strip carbon dioxide therefrom;
   recycling the absorption solution to said contacting with the gaseous stream; and
   introducing gas recovered from the carbon dioxide absorption and chlorinated hydrocarbon stripping into the chlorinated hydrocarbon production zone.

2. The process of claim 1 wherein a hydrocarbon stripping gas is employed to effect the stripping of chlorinated hydrocarbon from the absorption solution, said hydrocarbon stripping gas being a hydrocarbon employed as feed to the chlorinated hydrocarbon production zone, with the hydrocarbon stripping gas and stripped chlorinated hydrocarbon being introduced into the chlorinated hydrocarbon production zone.

3. The process of claim 2 wherein the hydrocarbon employed as feed and as stripping gas is methane.

4. The process of claim 3 wherein the carbon dioxide absorption solution is a carbonate.

5. The process of claim 4 wherein the carbon dioxide absorption is affected at a temperature of from 110° F to 160° F and as pressure of from 50 to 500 psig.

6. The process of claim 5 wherein the carbonate is potassium carbonate.

7. The process of claim 2 wherein the hydrocarbon employed as feed and as stripping gas is selected from the group consisting of ethane, ethylene and mixtures thereof.

8. The process of claim 7 wherein the carbon dioxide absorption solution is a carbonate.

9. The process of claim 8 wherein the carbonate is potassium carbonate.

10. The process of claim 2 wherein the stripping and carbon dioxide absorption are effected in a single vessel, with the hydrocarbon stripping gas and stripped chlorinated hydrocarbon being withdrawn from the vessel with the gas recovered from the carbon dioxide absorption.

* * * * *